(12) United States Patent
Rourke et al.

(10) Patent No.: US 7,041,129 B2
(45) Date of Patent: *May 9, 2006

(54) MICRO-POROUS MESH STENT WITH HYBRID STRUCTURE

(75) Inventors: Jonathan M. Rourke, Los Altos, CA (US); Yi Yang, San Francisco, CA (US)

(73) Assignee: Endotex Interventional Systems, Inc, Cupertino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/719,228

(22) Filed: Nov. 21, 2003

(65) Prior Publication Data

US 2004/0111142 A1   Jun. 10, 2004

Related U.S. Application Data

(63) Continuation of application No. 09/929,474, filed on Aug. 13, 2001, now Pat. No. 6,676,701, which is a continuation of application No. 09/495,827, filed on Feb. 1, 2000, now Pat. No. 6,312,463.

(51) Int. Cl.
*A61F 2/04* (2006.01)

(52) U.S. Cl. ........................... 623/1.39; 623/1.2

(58) Field of Classification Search ................ 606/194, 606/198, 200; 623/1.15, 1.18, 1.39, 1.2, 623/1.4

See application file for complete search history.

(56) References Cited

U.S. PATENT DOCUMENTS

| | | |
|---|---|---|
| 5,078,736 A | 1/1992 | Behl |
| 5,441,515 A | 8/1995 | Khosravi et al. |
| 5,443,500 A | 8/1995 | Sigwart |
| 5,609,627 A | 3/1997 | Goicoechea et al. |
| 5,720,735 A | 2/1998 | Dorros |

(Continued)

FOREIGN PATENT DOCUMENTS

WO    WO 98/11857 A    3/1998

(Continued)

OTHER PUBLICATIONS

PCT Publication No. WO 99/07308, "Microporous Stent and Implantation Device," Feb. 18, 1999.

(Continued)

*Primary Examiner*—Cary E. O'Connor
(74) *Attorney, Agent, or Firm*—Orrick Herrington & Sutcliffe, LLP (57) ABSTRACT

A prosthesis for treating a body passage includes a microporous tubular element and a support element. The tubular element is formed from a thin-walled sheet having a wall thickness of 25 micrometers or less, preferably a coiled-sheet exhibiting temperature-activated shape memory properties. The mesh pattern includes a plurality of openings in the sheet having a maximum dimension of not more than about 200 micrometers, thereby acting as a filter trapping embolic material while facilitating endothelial growth therethrough. The support element includes a plurality of struts, preferably having a thickness of 100–150 micrometers. The support element is preferably an independent component from the tubular element. Alternatively, the support element may be attached to or integrally formed as part of the tubular element. The tubular and support elements are placed on a catheter in contracted conditions and advanced endoluminally to a treatment location within a body passage. The tubular element is deployed, and the support element is expanded to an enlarged condition at the treatment location to engage an interior surface of the tubular element, thereby securing the tubular element and holding the lumen of the treatment location open.

7 Claims, 3 Drawing Sheets

U.S. PATENT DOCUMENTS

| | | |
|---|---|---|
| 5,800,517 A | 9/1998 | Anderson et al. |
| 5,824,053 A | 10/1998 | Khosravi et al. |
| 5,824,054 A | 10/1998 | Khosravi et al. |
| 5,827,322 A | 10/1998 | Williams |
| 5,895,407 A * | 4/1999 | Jayaraman ................... 623/1.2 |
| 5,972,027 A | 10/1999 | Johnson |
| 5,980,554 A | 11/1999 | Lenker et al. |
| 5,980,565 A | 11/1999 | Jayaraman |
| 6,004,347 A | 12/1999 | McNamara et al. |
| 6,015,433 A | 1/2000 | Roth |
| 6,048,360 A | 4/2000 | Khosravi et al. |
| 6,096,175 A * | 8/2000 | Roth ..................... 204/192.15 |
| 6,110,198 A | 8/2000 | Fogarty |
| 2001/0039449 A1 | 11/2001 | Johnson et al. |

FOREIGN PATENT DOCUMENTS

| | | |
|---|---|---|
| WO | WO 98/22045 A | 5/1998 |
| WO | WO 98/25544 A | 6/1998 |
| WO | WO 00/61034 A | 10/2000 |

OTHER PUBLICATIONS

EPO Publication No. EP 0 875 218 A2, "Porous Medicated Stent," Apr. 15, 1998.

PCT Publication No. WO 99/62432, "Endovascular Thin Film Devices and Methods for Treating and Preventing Stroke," Dec. 9, 1999.

* cited by examiner

MICRO-POROUS MESH STENT WITH HYBRID STRUCTURE

RELATED INFORMATION

This application is a continuation of application Ser. No. 09/929,474, filed Aug. 13, 2001, now U.S. Pat. No. 6,676,701, which is a continuation of application Ser. No. 09/495,827, filed Feb. 1, 2000, now U.S. Pat. No. 6,312,463, the disclosure of which is expressly incorporated herein by reference.

FIELD OF THE INVENTION

The present invention relates generally to endoluminal prostheses or "stents," and more particularly to stents including a micro-porous mesh structure supported by an integral or separate strut structure, and to methods of making and deploying such stents.

BACKGROUND

Tubular prostheses or "stents" are often implanted within blood vessels, for example, within the coronary and carotid arteries, for treating atherosclerotic disease that may involve one or more stenoses. Stents generally have a tubular shape capable of assuming a radially contracted condition to facilitate introduction into a patient's vasculature, and an enlarged condition for engaging the vessel wall at a treatment location.

Plastically deformable stents have been suggested that are initially provided in their contracted condition, and placed over a balloon on an angioplasty catheter. At the treatment location, the balloon is inflated to plastically deform the stent until it is expanded to its enlarged condition.

Self-expanding stents have also been suggested that are biased to assume an enlarged condition but may be radially compressed to a contracted condition. The stent may be mounted to a delivery device and constrained in the contracted condition during delivery, for example, by an overlying sheath. At the treatment location, the stent may be released, for example, by retracting the sheath, the stent automatically resuming its enlarged condition to engage the vessel wall.

In addition to tubular stents, coiled-sheet stents have been suggested that include a flat sheet rolled into a spiral or helical shape having overlapping inner and outer longitudinal sections. Such stents generally have a lattice-like structure formed in the sheet and a plurality of fingers or teeth along the inner longitudinal section for engaging openings in the lattice. Once deployed at a treatment location, the fingers may engage openings in the lattice to lock the stent in the enlarged condition.

One of the problems with many stent structures, whether balloon-expandable or self-expanding, is that they substantially expose the underlying wall of the treatment location. For example, helical wire stent structures generally have substantial gaps between adjacent turns of the wire. Multicellular stent structures, which may include a series of slotted or zig-zag-shaped cells, create large spaces within and/or between the cells, particularly as they expand to their enlarged condition. The lattice structure of coiled-sheet stents generally also includes relatively large openings.

Thus, despite holding the wall of the treatment location generally open, the openings or gaps in these stents may substantially expose the bloodstream to plaque, tissue prolapse, or other embolic material attached to the wall of the vessel. This embolic material may be inadvertently released during or after deployment of the stent, and then travel downstream where it may cause substantial harm, particularly if it reaches a patient's neurovasculature.

One proposed solution to address the issue of embolic containment is to cover a conventional stent with a fabric or polymer-type material. This solution has met with limited success, however, because of the propensity to form false lumens due to poor apposition of the covering and the vessel wall.

Accordingly, it is believed that a stent capable of supporting the wall of a blood vessel being treated, while substantially minimizing exposure of embolic material to the bloodstream, would be considered useful.

SUMMARY OF THE INVENTION

The present invention is directed to an endoluminal prosthesis or "stent" including a micro-porous mesh structure and a support structure, and to methods of making and implanting such stents. In accordance with one aspect of the present invention, a micro-porous mesh structure for supporting a wall of a body passage is provided that includes a generally tubular body having a contracted condition for facilitating delivery into the body passage, and an enlarged condition for engaging the wall of the body passage, the tubular body having a preferred wall thickness of not more than about 25 micrometers (0.001 inch). A plurality of openings are provided in the tubular body defining a mesh pattern therein, each opening preferably having a maximum dimension of not more than about 200 micrometers (0.008 inch).

In a preferred form, the tubular body is a coiled-sheet having overlapping inner and outer sections formed from a material, such as Nitinol, exhibiting temperature-activated shape memory properties. A plurality of struts may be formed integrally onto the tubular body and spaced along a length of the tubular body for supporting the tubular body against the wall of the body passage, having, for example, a thickness of about 100–150 micrometers (0.004–0.006 inch).

In accordance with another aspect of the present invention, a prosthesis for supporting a wall of a body passage is provided that includes a tubular element, such as the micro-porous mesh structure described above, and a separate support element including a plurality of struts for engaging an interior surface of the tubular element. The support element is preferably biased to an enlarged condition at body temperature for substantially securing the tubular element against the wall of the body passage in the enlarged condition. The support element may be any of a variety of known stent strictures, such as a coiled-sheet stent, preferably formed from a material, such as Nitinol, exhibiting temperature-activated shape memory properties.

In accordance with yet another aspect of the present invention, a method for making a prosthesis for supporting a wall of a body passage includes providing a sheet formed from a shape memory alloy, preferably having a transition temperature between a substantially ambient temperature and body temperature, the sheet having a wall thickness of not more than about 25 micrometers (0.001 inch). A mesh pattern is formed in the sheet that includes a plurality of micro-porous openings, and the sheet is formed into a generally tubular body, for example, by rolling it into a coiled-sheet having overlapping inner and outer sections.

The tubular body may be heat treated at a first temperature substantially higher than the transition temperature to program an expanded condition for engaging the wall of the body passage into the shape memory material. The tubular body may then be cooled to a second temperature below the transition temperature, and compressed into a contracted condition for facilitating delivery into the body passage.

In one preferred form, the sheet has an initial wall thickness greater than about 25 micrometers (0.001 inch) and not more than about 150 micrometers (0.006 inch). Portions of the sheet are removed to provide a plurality of struts having a thickness similar to the initial wall thickness separating thin-walled regions having a final wall thickness of not more than about 25 micrometers (0.001 inch). In another preferred form, a separate strut element may be provided for supporting the tubular body that may be attached to the tubular body.

In accordance with still another aspect of the present invention, a method for supporting a wall of a predetermined location within a body passage incorporates a prosthesis including a micro-porous tubular element and a separate support element, such as that described above. The tubular and support elements are placed in contracted conditions on a distal region of a delivery device, such as a catheter. The distal region of the delivery device is advanced endoluminally within the body passage to the predetermined location. The tubular element is deployed at the predetermined location, and the support element is expanded to an enlarged condition to engage an interior surface of the tubular element, thereby substantially securing the tubular element against the wall of the predetermined location.

Preferably, the support element is biased to expand to its enlarged condition at body temperature such that upon deployment from the delivery device, the support element automatically expands to engage the interior surface of the tubular element. The tubular element may be expanded to an enlarged condition as the support element expands to its enlarged condition, or alternatively, the tubular element may also be biased to expand to an enlarged condition at body temperature such that the tubular element automatically expands to its enlarged condition to conform to the wall of the predetermined location upon deployment from the delivery device.

Thus, a prosthesis in accordance with the present invention may be used to treat a stenosis within a blood vessel, such as within the carotid, coronary or cerebral arteries. The tubular element may substantially trap embolic material against the wall of the vessel once secured by the support element, while the micro-porous mesh pattern facilitates endothelial growth, thereby substantially reducing the risk of releasing embolic material into the bloodstream. Also, the provision of a micro-porous mesh structure and a separate support structure may allow the support structure to slide along the surface of the tubular element without significantly disturbing the underlying diseased vessel wall.

In addition, in a preferred embodiment, the micro-porous mesh structure is biased to its enlarged condition such that the tubular body may tend to expand out to engage the vessel wall. Thus, the micro-porous mesh structure may contact the vessel wall at points between the struts of the support structure, thereby minimizing the creation of false lumens or other gaps between the micro-porous mesh structure and the vessel wall.

Other objects and features of the present invention will become apparent from consideration of the following description taken in conjunction with the accompanying drawings.

DETAILED DESCRIPTION OF THE PREFERRED EMBODIMENTS

Figure 1:
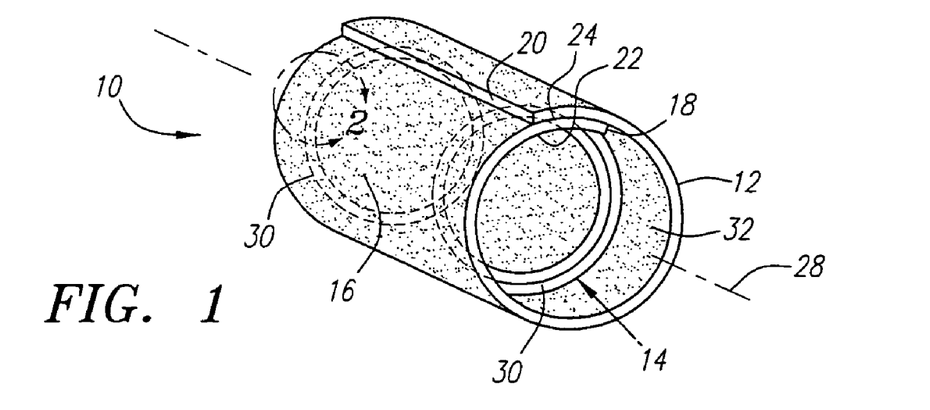
FIG. 1 is a perspective view of a first preferred embodiment of a two-stage stent in accordance with the present invention, including a micro-porous tubular element and a support element.

Turning now to the drawings, FIG. 1 shows a first preferred embodiment of a stent 10 in accordance with the present invention. Generally, the stent 10 includes two elements, namely a micro-porous tubular element 12 and a support element 14. Both elements 12, 14 have a contracted condition for facilitating introduction into a body passage, such as a patient's vasculature, and an enlarged condition for engaging the wall of a treatment location, such as a stenotic region of a blood vessel.

The micro-porous tubular element 12 is preferably formed from a shape memory alloy, such as Nitinol, having a plurality of openings 16 defining a micro-porous mesh pattern therein. The mesh pattern is "micro-porous" in that the openings 16 are sufficiently small such that they substantially prevent plaque or other embolic material from extending through the openings 16. Thus, the tubular element 12 may behave as a filter, allowing endothelial growth to occur through the openings 16 while substantially protecting the patient from the release of embolic material through the mesh pattern. Openings 16 having a maximum open dimension of not more than about 400 micrometers (0.016 inch) are preferred to provide an effective micro-porous mesh pattern, with openings between about 80 micrometers (0.003 inch) and about 200 micrometers (0.008 inch) being more preferred.

Figure 2:
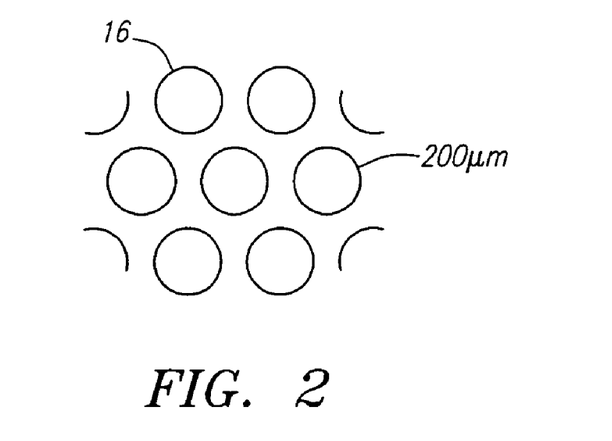
FIG. 2 is a detail of the wall of the tubular element of FIG. 1, showing a first preferred form of a micro-porous mesh pattern therein.

Turning to FIG. 2, in a preferred form, the mesh pattern includes a staggered pattern of substantially circular openings 16 in the shape memory alloy material. The openings 16 are preferably spaced apart from one another such that the resulting tubular element 12 has a surface coverage of not more than about 20 percent, i.e., not more than about 20 percent of the overall surface area of the vessel wall covered by the tubular element 12 is directly engaged with stent material. This relatively low percentage of remaining stent material after formation of the mesh pattern may enhance the flexibility of the tubular element 12, thereby facilitating its conformance with the wall of a treatment location, as well as facilitating delivery through tortuous anatomy. Alternatively, other opening shapes may be provided, such as diamonds, triangles, rectangles, or ovals. An important feature of the openings 16 is that they are not likely to over-expand when the tubular element 12 is expanded to its enlarged condition, which may otherwise increase the risk of embolic material being exposed or escaping through them.

Returning to FIG. 1, the tubular element 12 preferably has a coiled-sheet configuration. The tubular element 12 is formed from a flat sheet (not shown), preferably having a wall thickness of not more than about 25 micrometers (0.001 inch). The plurality of openings 16 are formed in the flat sheet, for example, by laser drilling, etching or other known processes. The openings 16 may be arranged substantially uniformly along the length of the flat sheet, or alternatively, the spacing, shape and/or size of the openings 16 may be varied in a predetermined manner along the length of the flat sheet to create desired properties in the finished tubular element 12, e.g., a desired transverse flexibility, expansion bias, compressibility, etc. that varies along the length of the resulting tubular element 12.

The flat sheet is then rolled into a coiled-sheet having overlapping inner and outer sections 22, 24. In one preferred form, the inner and outer sections 22, 24 define a longitudinal seam 26 between them that extends substantially parallel to a longitudinal axis 28 of the tubular element 12. Alternatively, the inner and outer sections may be overlapped such that they define a helical seam between them that extends down a length of the tubular element 12 (not shown). In the latter alternative, the flat sheet may have a generally parallelogram shape rather than a rectangular shape.

Preferably, the sheet is formed from a nickel-titanium alloy ("Nitinol"), or other shape memory alloy, and more preferably from a material exhibiting temperature-activated shape memory properties. For example, the material may have a transition temperature between substantially ambient temperatures and body temperature. Thus, at substantially ambient temperatures, for example, below about 25 degrees Celsius, the material may be substantially martensitic, while at body temperature, for example, at or above 37 degrees Celsius, the material may be substantially austenitic.

The coiled-sheet may be formed into a desired size and shape, preferably into a desired enlarged condition for engaging a predetermined sized lumen of a blood vessel. For example, the coiled-sheet may be formed into a generally cylindrical shape having a diameter of between about 2 mm and about 14 mm, depending upon the size of the target lumen. The coiled-sheet may then be heat treated at temperatures substantially higher than body temperature, for example, at a temperature of about 600 degrees Celsius or higher, for a predetermined time to program the size and shape into the material's shape memory.

The coiled-sheet may then be cooled below its transition temperature, for example, to a temperature of about zero degrees Celsius or less. At this temperature, the coiled-sheet is preferably radially compressed to its contracted condition, i.e., compressed in-plane, and also coiled, to achieve dense packing. Compressing the coiled-sheet in-plane involves elastically deforming the sheet itself, i.e., compressing the coiled-sheet material about its longitudinal axis, thereby compressing the plurality of openings 16 defining the mesh pattern. In the contracted condition, the openings 16 may thus be partially closed in a direction about the circumference of the coiled-sheet. After packing, the coiled-sheet may be compressed by about three hundred percent or more, i.e., the circumferential dimension of the coiled-sheet in the contracted condition may be about one third or less than in the enlarged condition. The sheet is also preferably coiled further, possibly creating multiple overlapping sections. When the coiled-sheet is coiled in this manner, it may retain its contracted condition, or it may remain biased to at least partially unwind.

The coiled-sheet may then be placed on a delivery device, such as a catheter having an overlying sheath or other constraint, as described more particularly below. When the delivery device is introduced into a patient's vasculature, the coiled-sheet becomes exposed to body temperature, i.e., to a temperature above its transition temperature, causing the material to return to its austenitic phase. This activates the Nitinol material's shape memory, biasing the coiled-sheet towards its enlarged condition. When deployed from the delivery device, the coiled-sheet may at least partially expand towards the enlarged condition, preferably to substantially conform to the wall of the vessel at the deployment site.

Although the tubular element 12 is preferably self-supporting, because of the relatively thin wall thickness of the sheet, the tubular element 12 may not be sufficiently strong to support the diseased vessel. For this reason, the inner longitudinal edge 18 of the coiled-sheet generally may not include teeth or fingers, as provided on conventional coiled-sheet stents. The primary purpose of the tubular element 12 is to conform to and substantially cover the wall of the vessel at a treatment location and trap any embolic material between the tubular element 12 and the wall of the vessel. Locking fingers and the like may interfere with this conformability and/or with the ability of the coiled-sheet to unroll during deployment, as may irregularly shaped openings in the mesh pattern. Therefore, it is generally preferred that the coiled-sheet have a substantially smooth wall, thereby enhancing the unrolling of the coiled-sheet and its conformance with an irregular vessel wall.

Returning to FIG. 1, the support element 14 generally provides structural support for holding the tubular element 12 against the vessel wall and holding the lumen of the vessel open. The support element 14 includes a plurality of struts 30 spaced apart along the longitudinal axis 28 for engaging an interior surface 32 of the tubular element 12. The struts 30 preferably have a thickness of between about 100 micrometers (0.004 inch) and about 150 micrometers (0.006 inch). In a first preferred form, the support element 14 is biased to its enlarged condition at body temperature, similar to the temperature-activated shape memory material described above for the tubular element 12, such that the support element 14 may substantially secure the tubular element 12 against the wall of a vessel in its enlarged condition, as described further below. Alternatively, the support element 14 may be plastically deformable from its contracted condition to its enlarged condition.

The structure of the support element 14 may take a variety of forms. Known and/or commercially available stents may be appropriate for use as a support element for the microporous tubular element 12 described above. For example, the support element 14 may be a coiled-sheet stent having a lattice structure (not shown), such as those disclosed in U.S. Pat. No. 5,443,500 issued to Sigwart, or U.S. Pat. No. 5,007,926 issued to Derbyshire, the disclosures of which are expressly incorporated herein by reference. Alternatively, the support element 14 may be a helical wire stent, such as those disclosed in U.S. Pat. No. 4,665,918 issued to Garza et al. or U.S. Pat. No. 4,553,545 issued to Maass et al., a wire mesh stent, such as those disclosed in U.S. Pat. No. 5,871, 538 issued to Dereume or U.S. Pat. No. 5,221,261 issued to Termin et al., a multi-cellular slotted stent, such as those disclosed in U.S. Pat. Nos. 4,733,665 or 4,739,762 issued to Palmaz, or a zig-zag stent, such as those disclosed in U.S.

Pat. No. 4,580,568 issued to Gianturco, or U.S. Pat. No. 5,843,120 issued to Israel et al. The disclosure of these patents and any others referenced therein are expressly incorporated herein by reference. Other known stent structures (not shown) may also be used which, for example, substantially engage the interior of the tubular body 12 and provide sufficient support for the wall of the body passage.

In one form, the support element 14 may be attached directly to the tubular element 12. For example, the struts 30 of the support element 14 may be substantially permanently attached continuously or at discrete locations where they contact the interior surface 32 of the tubular element 12, e.g., using an adhesive or by welding. Thus, the tubular element 12 and support element 14 may be provided as a single unit that is mounted on a delivery device and deployed together at a treatment location.

More preferably, the support element 14 is provided separate from the tubular element 12, and the two elements 12, 14 are deployed independently from one another. Thus, the stent 10 may be deployed in a two-stage method for supporting a wall of a predetermined location, such as a stenosis, within a blood vessel or other body passage, for example, within the renal, iliac, femoral arteries, and preferably within the carotid, cerebral or coronary arteries. In addition, the stent 10 may be implanted within a degenerated bypass graft within one of these arteries.

Figure 4A:
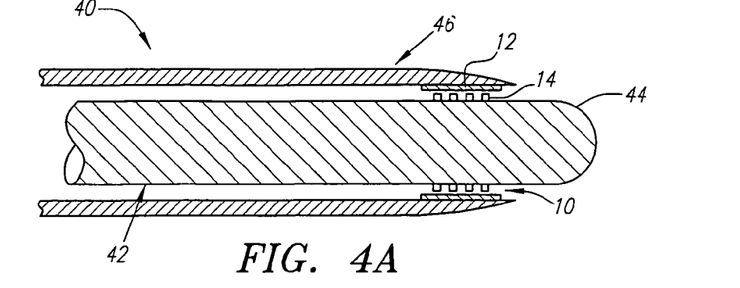
FIG. 4A is a cross-sectional view of a distal region of a delivery device with a stent in accordance with the present invention mounted thereon.

Initially, as shown in FIG. 4A, the tubular and support elements 12, 14 are placed in their contracted conditions on a distal region of a delivery device 49. The delivery device 40 preferably includes a catheter 42 having a proximal end (not shown) and a distal end 44 having a size and shape for facilitating introduction into a patient's vasculature. The delivery device 40 also preferably includes a tubular sheath 46 that may be advanced over the distal end 44 of the catheter 42 to constrain the tubular and support elements 12, 14 in their contracted conditions. In a preferred form, the tubular element 12 is placed concentrically over the support element 14 on the distal end 44 of the catheter 42. Alternatively, the tubular element 12 and the support element 14 may be placed adjacent one another on the distal end of the catheter (not shown).

In addition to or instead of the sheath 46, other constraints (not shown) may be associated with the delivery device 40 for securing the tubular and support elements 12, 14 axially on the distal end 44 of the catheter 42 and/or for preventing premature expansion of the tubular and support elements 12, 14 from their contracted conditions. For example, one or more wire elements (not shown) may be extended through lumens (also not shown) in the catheter 42 from the proximal end that may be detachably connected to the tubular or support elements 12, 14. The wire elements may be woven through apertures (not shown) in the tubular or support elements 12, 14 and subsequently withdrawn at time of deployment, similar to those shown and described in U.S. Pat. No. 5,824,053 issued to Khosravi et al., the disclosure of which is expressly incorporated herein by reference.

Figure 4B:
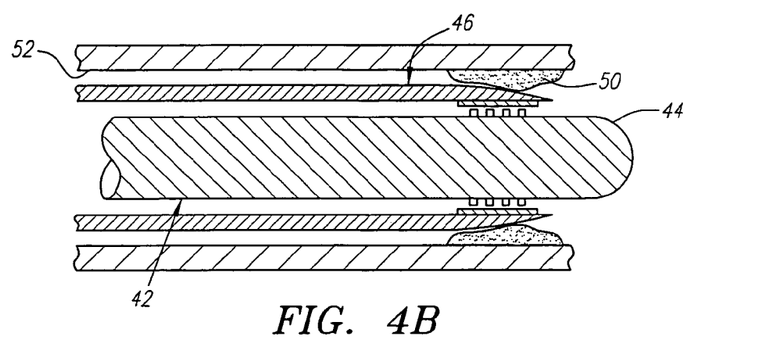
FIGS. 4B–4D are cross-sectional views, showing the delivery device and stent of FIG. 4A being directed to a treatment location within a body passage where the stent is implanted.

The distal end 44 of the catheter 42 may then be percutaneously introduced into a peripheral vessel of a patient (not shown), such as the femoral artery, and advanced endoluminally through the patient's vasculature to a predetermined treatment location, such as a stenotic or occluded region 50 within a blood vessel 52, as shown in FIG. 4B. An angioplasty, atherectomy or other similar procedure may have been previously performed at the treatment location 50 to open the treatment location 50 or otherwise prepare the location 50 for implantation of the stent 10.

Figure 4C:
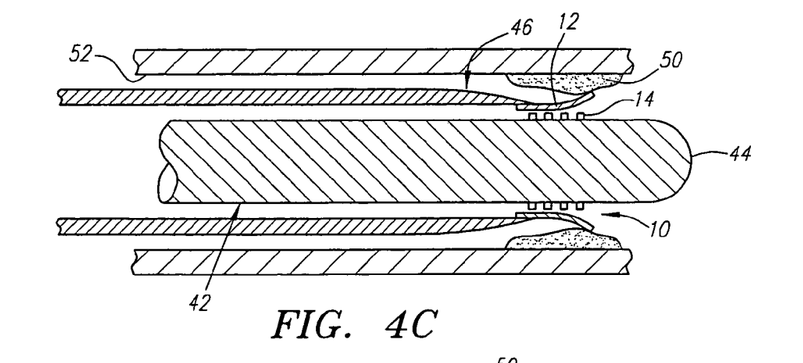

As shown in FIG. 4C, the tubular element 12 may be placed across the treatment location 50 and deployed, for example, by withdrawing the sheath 46 or other constraints securing it to the delivery device 40. Preferably, the tubular element 12 is self-expanding, i.e., is biased to expand towards its enlarged condition, for example, by providing the tubular element 12 from a shape memory material, such as the temperature-activated Nitinol previously described. Thus, when the tubular element 12 is released from the delivery device 40, it automatically expands to its enlarged condition to conform substantially to the size and shape of the wall of the treatment location 50. Alternatively, the tubular element 12 may only partially expand or may require a balloon or other expandable member on the catheter or a separate device (not shown) to expand it to its enlarged condition.

Figure 4D:
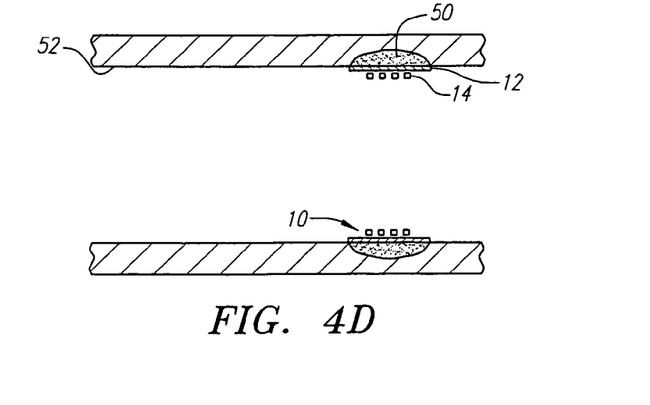

The support element 14 may be released simultaneously with the tubular element 12, e.g., when the sheath is withdrawn from the distal end 44 of the catheter 42. Alternatively, the delivery device 40 may include additional constraints (not shown) that may secure the support element 14 independently of the tubular element 12 to allow successive deployment of the support and tubular elements 12, 14. The support element 14 is also preferably self-expanding, i.e., is biased to expand to substantially engage the wall of the treatment location 50 and hold the lumen of the vessel 52 substantially open. Thus, when the support element 14 is released from the catheter 42, it may automatically expand to its enlarged condition to engage the interior surface 32 of the tubular element 12, thereby substantially securing the tubular element 12 against the wall of the vessel 50 at the treatment location 50 and holding the lumen of the vessel 52 substantially open, as shown in FIG. 4D.

Where the tubular and support elements 12, 14 are both self-expanding and simultaneously deployed, the tubular element 12 may be biased to expand more rapidly than the support element 12, thereby ensuring that the tubular element 12 conforms to the size and/or shape of the treatment location 50 before being substantially secured by the support element 14 against the wall thereof. Where the support element 14 is self-expanding and the tubular element 12 is not, the tubular element 12 may be expanded to its enlarged condition as the support element 14 is deployed and automatically expands to its enlarged condition. Stated differently, the support element 14 may provide sufficient radially outward force to expand the tubular element 12, for example, to cause a coiled-sheet tubular element 12 to unroll and conform to the cross-section of the vessel 52.

Once deployed, the Support element 14 substantially secures the tubular element 12 against the wall of the vessel 52 and preferably provides sufficient radial support to hold the lumen of the vessel 52 substantially open. The tubular element 12 substantially traps any embolic material attached to the wall of the treatment location 52 against the wall of the vessel 50. Thus, the patient may be substantially protected from the release of embolic material during or after deployment that might otherwise travel downstream and potentially cause substantial harm, particularly within the arteries leading to the brain. Because of the micro-porous mesh pattern, however, the stent 10 continues to allow endothelial growth through the tubular element 12.

Generally, friction may sufficiently maintain the relative position of the tubular and support elements 12, 14 within the vessel. More preferably, the support element 14 may slidably engage the interior surface 32 of the tubular element 12, thereby accommodating some natural adjustment of the stent 10 after deployment. Alternatively, the support element 14 may be attached to the tubular element 12 during deployment, for example, using an adhesive on the interior surface 32 of the tubular element 12 or the support element 14.

Figure 3:
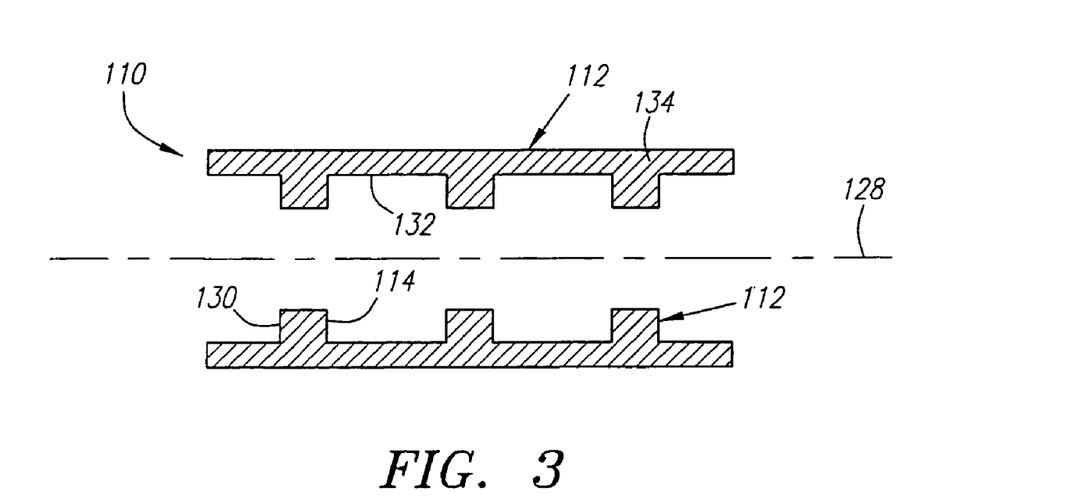
FIG. 3 is a cross-sectional view of a second preferred embodiment of a stent including a micro-porous tubular element with an integral support element.

Turning to FIG. 3, a second preferred embodiment of a hybrid stent 110 is shown that includes a support element 114 that is integrally formed with a tubular element 112. Generally, the tubular element 112 is similar to the separate tubular element 12 described above. Instead of a separate support element 14, however, a plurality of struts 130 may be formed directly from the sheet material of the tubular element 112. The struts 130 may simply be annular shaped members that extend substantially around the circumference of the tubular element 112, or a more complicated strut design (not shown) may be formed to provide predetermined structural properties, such as enhanced transverse flexibility, as will be appreciated by those skilled in the art. The struts 130 may extend from an interior surface 132 of the tubular element 112, as shown, may extend from an exterior surface (not shown), or alternatively may be formed along either or both of the interior and exterior surfaces.

In a preferred method for making the hybrid stent 110, a flat sheet, preferably formed from a shape memory material, such as the temperature-activated Nitinol described above, is provided having a predetermined initial thickness. In a preferred form, the initial thickness of the flat sheet is the desired thickness of the struts defining the support element 114. For example, a flat sheet having a thickness of between about 100 micrometers (0.004 inch) and about 150 micrometers (0.006 inch) may be provided.

Material is then selectively removed from a surface of the flat sheet, for example, using an etching process, to thin predetermined regions 134 of the flat sheet, preferably to a desired thickness of the tubular element 112, e.g., not more than about 25 micrometers (0.001 inch). Thus, after the removal process, a plurality of struts 130 remain having a thickness similar to the initial wall thickness that separate relatively thin-walled regions 134 defining the tubular element 112. A mesh pattern (not shown) may be formed in the thin-walled regions 134, and then the flat sheet may be formed into a coiled-sheet and/or heat treated, similar to the previously described embodiment.

The stent 110 may then be placed on a delivery device, similar to the catheter and sheath described above, delivered into a patient's body passages, and implanted at a predetermined treatment location, similar to the methods described above.

Figure 5:
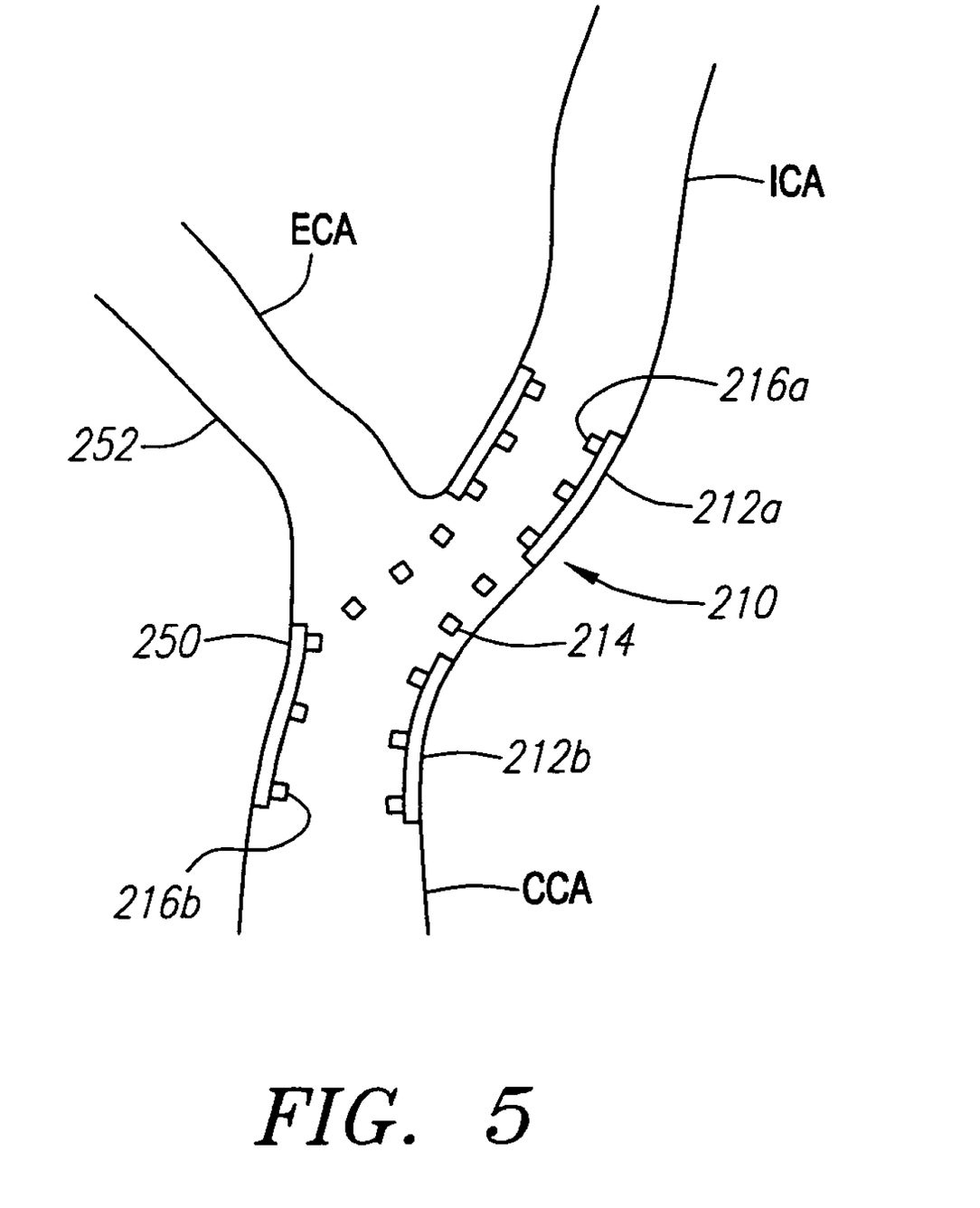
FIG. 5 is a cross-sectional view of a bifurcation between main and branch vessels across which a third preferred embodiment of a stent in accordance with the present invention is implanted.

Turning to FIG. 5, another preferred embodiment of a multiple-stage stent 210 in accordance with the present invention is shown that may be implanted across a bifurcation between a main vessel 250 and a branch vessel 252, such as the common carotid artery (CCA), the internal carotid artery (ICA), and the external carotid artery (ECA). The stent 210 generally includes a pair of micro-porous tubular elements 212a, 212b and a single support element 214, similar to the embodiments described above.

To implant the stent 210, the tubular elements 212a, 212b may be placed on a distal portion of a delivery device, such as a catheter similar to that described above (not shown). Preferably, the tubular elements 212a, 212b are spaced apart axially from one another on the distal portion by a predetermined distance, such as a distance corresponding substantially to the size of the branch vessel 252, e.g. at least about 5 mm and more preferably 10 mm or more. Alternatively, the tubular elements 212a, 212b may be mounted adjacent one another and successively deployed at a treatment location. A sheath and/or other constraints (not shown) may be used to secure the tubular elements 212a, 212b on the delivery device.

The support element 214 may be provided on the delivery device under the tubular elements 212a, 212b, similar to the embodiments described above. Alternatively, the support element 214 may be mounted on the delivery device proximate the tubular elements 212a, 212b to facilitate successive delivery of the tubular and support elements 212, 214. In a further alternative, the support element 214 may be mounted on a separate delivery device.

With the tubular and support elements 212, 214 thereon, the distal portion of the delivery device may be percutaneously introduced into a peripheral vessel and advanced into the main vessel 250 until the tubular elements 212a, 212b straddle the branch vessel 252. The tubular elements 212a, 212b may then be deployed, for example, by withdrawing the overlying sheath, the tubular elements 212a, 212b preferably automatically expanding to conform to the wall of the main vessel 250 on either side of the branch vessel 252. Alternatively, the distal tubular element 212a may be positioned and deployed first distal (e.g. downstream) of the bifurcation, and then the proximal tubular element 212b may be positioned and deployed proximal (e.g. upstream) of the bifurcation. The catheter and/or tubular elements 212a, 212b may include radiopaque markers and the like, allowing a physician to externally visualize the tubular elements 212a, 212b, for example, using fluoroscopy, to position the tubular elements 212a, 212b relative to the bifurcation before deployment.

The support element 214 may be deployed simultaneously with the tubular elements 212a, 212b or may be separately constrained on the delivery device and deployed subsequent to the tubular elements 212a, 212b. If separately deployed, the support element 214 may be positioned within the main vessel 250 until the support element 214 spans the branch vessel 252 with respective end regions 216a, 216b of the support element being located within the interior of the tubular elements 212a, 212b. The support element 214 may be expanded to substantially engage the tubular elements 212a, 212b and hold the lumen of the main vessel 250 open.

The length of the support element 214 preferably corresponds substantially to the length of the tubular elements 212a, 212b and the space between them. For example, if tubular elements 212a, 212b having a length of about 15 mm are to be implanted that are spaced apart from one another by about 10 mm, the support element 214 should have a length of about 40 mm.

Once implanted, the stent 210 substantially supports the lumen of the main vessel 250, the tubular elements 212a, 212b substantially trapping embolic material against the wall of the main vessel 250. The space between the tubular elements 212a, 212b allows substantially unobstructed blood flow through the branch vessel 252, because of the relatively large openings, i.e., open-celled structure, in the support element 214. In an alternative method, the stent 210 may be implanted to extend from the main blood vessel 250 into the branch vessel 252 (not shown) in a similar method to that described, as will be appreciated by those skilled in the art.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A micro-porous mesh structure for supporting a wall of a body passage, comprising:
   a non-polymeric, non-silicone generally tubular body having a contracted condition for facilitating delivery into the body passage, and an enlarged condition for engaging the wall of the body passage, the tubular body being biased to its enlarged condition, the tubular body having a plurality of openings defining a micro-porous mesh pattern therein; and
   a support element that slidably engages the tubular body in the enlarged condition.

2. A micro-porous mesh structure for supporting a wall of a body passage, comprising:
   a non-polymeric, non-silicone generally tubular body having a contracted condition for facilitating delivery into the body passage, and an enlarged condition for engaging the wall of the body passage, the tubular body being biased to its enlarged condition, the tubular body having a plurality of openings defining a micro-porous mesh pattern therein; and
   a support element that is attachable to the tubular body during deployment.

3. A micro-porous mesh structure for supporting a wall of a body passage, comprising:
   a non-polymeric, non-silicone generally tubular body having a contracted condition for facilitating delivery into the body passage, and an enlarged condition for engaging the wall of the body passage, the tubular body being biased to its enlarged condition, the tubular body having a plurality of openings defining a micro-porous mesh pattern therein; and
   a support element that is substantially permanently attached to the interior surface of the tubular body.

4. A micro-porous mesh structure for supporting a wall of a body passage, comprising:
   a non-polymeric, non-silicone generally tubular body having a contracted condition for facilitating delivery into the body passage, and an enlarged condition for engaging the wall of the body passage, the tubular body being biased to its enlarged condition, the tubular body having a plurality of openings defining a micro-porous mesh pattern therein; and
   a support element having a wall thickness of not more than about 150 micrometers (0.006 inch).

5. A micro-porous mesh structure for supporting a wall of a body passage, comprising:
   a non-polymeric, non-silicone generally tubular body having a contracted condition for facilitating delivery into the body passage, and an enlarged condition for engaging the wall of the body passage, the tubular body being biased to its enlarged condition, the tubular body having a plurality of openings defining a micro-porous mesh pattern therein; and
   a support element comprising a coiled-sheet having overlapping inner and outer sections.

6. A micro-porous mesh structure for supporting a wall of a body passage, comprising:
   a non-polymeric, non-silicone generally tubular body having a contracted condition for facilitating delivery into the body passage, and an enlarged condition for engaging the wall of the body passage, the tubular body being biased to its enlarged condition, the tubular body having a plurality of openings defining a micro-porous mesh pattern therein; and
   a support element comprising a shape memory alloy.

7. The micro-porous mesh structure of claim 6, wherein the shape memory alloy has a transition temperature between substantially ambient temperatures and body temperature, whereby the tubular element is biased to its enlarged condition when exposed to body temperature.

* * * * *